United States Patent
Wojcik et al.

(10) Patent No.: US 10,307,122 B2
(45) Date of Patent: *Jun. 4, 2019

(54) MODULAR ACCESSORY SLEEVE FOR PORTABLE RADIOGRAPHIC DETECTORS

(71) Applicant: CARESTREAM HEALTH, INC., Rochester, NY (US)

(72) Inventors: Timothy J. Wojcik, Rochester, NY (US); Jeffery R. Hawver, Marion, NY (US); Bradley S. Jadrich, North Port, FL (US)

(73) Assignee: Carestream Health, Inc., Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/828,946

(22) Filed: Dec. 1, 2017

(65) Prior Publication Data

US 2018/0085077 A1    Mar. 29, 2018

Related U.S. Application Data

(63) Continuation of application No. 14/387,248, filed as application No. PCT/US2013/036302 on Apr. 12, 2013, now Pat. No. 9,855,017.

(60) Provisional application No. 61/623,641, filed on Apr. 13, 2012.

(51) Int. Cl.
*A61B 6/00* (2006.01)
*G03B 42/04* (2006.01)
*G01T 1/24* (2006.01)

(52) U.S. Cl.
CPC .......... *A61B 6/4488* (2013.01); *A61B 6/4233* (2013.01); *A61B 6/4283* (2013.01); *A61B 6/4411* (2013.01); *A61B 6/547* (2013.01); *A61B 6/56* (2013.01); *G03B 42/04* (2013.01); *G01T 1/244* (2013.01); *Y10T 29/49826* (2015.01)

(58) Field of Classification Search
CPC .................................................... A61B 6/4283
See application file for complete search history.

(56) References Cited

U.S. PATENT DOCUMENTS

| | | |
|---|---|---|
| 7,495,226 B2 | 2/2009 | Jadrich et al. |
| 7,842,928 B2 | 11/2010 | Jadrich et al. |
| 7,924,980 B2 | 4/2011 | Ohta et al. |
| 7,989,773 B2 | 8/2011 | Jadrich et al. |
| 8,053,738 B2 | 11/2011 | Nishino et al. |
| 8,173,969 B2 | 5/2012 | Nishino et al. |
| 8,389,944 B2 | 3/2013 | Jadrich et al. |
| 8,829,455 B2 | 9/2014 | Nakatsugawa et al. |
| 9,855,017 B2 * | 1/2018 | Wojcik ................ A61B 6/4233 |
| 2007/0138400 A1 | 6/2007 | Ertel et al. |
| 2007/0272873 A1 | 11/2007 | Jadrich et al. |
| 2008/0240358 A1 | 10/2008 | Utschig et al. |
| 2009/0122959 A1 | 5/2009 | Jadrich et al. |

(Continued)

FOREIGN PATENT DOCUMENTS

KR    10-2012-010053 A    2/2012

OTHER PUBLICATIONS

International Search Report, International application No. PCT/US2013/036302, dated Jul. 26, 2013, 2 pages.

*Primary Examiner* — Thomas R Artman (57) ABSTRACT

Embodiments of methods and apparatus are disclosed that can provide a modular approach to an accessory shell for a portable DR detector that can accessorize features for various applications.

13 Claims, 11 Drawing Sheets (56) References Cited

U.S. PATENT DOCUMENTS

| | | |
|---|---|---|
| 2009/0220052 A1 | 9/2009 | Ohta et al. |
| 2010/0054399 A1 | 3/2010 | Nishino et al. |
| 2010/0072379 A1 | 3/2010 | Nishino et al. |
| 2010/0111263 A1 | 5/2010 | Lamberty et al. |
| 2010/0158197 A1 | 6/2010 | Jadrich et al. |
| 2011/0051902 A1 | 3/2011 | Liu et al. |
| 2011/0215250 A1 | 9/2011 | Ohta et al. |
| 2011/0272588 A1 | 11/2011 | Jadrich et al. |
| 2012/0153182 A1 | 6/2012 | Iwakiri |
| 2013/0228694 A1 | 9/2013 | Nakatsugawa et al. |
| 2015/0063550 A1 | 3/2015 | Wojcik et al. |
| 2017/0025761 A1* | 1/2017 | Kim .................. H01Q 9/42 |
| 2018/0085077 A1* | 3/2018 | Wojcik .............. A61B 6/4233 |
| 2018/0256122 A1* | 9/2018 | Wojcik .............. A61B 6/4283 |

\* cited by examiner

MODULAR ACCESSORY SLEEVE FOR PORTABLE RADIOGRAPHIC DETECTORS

CROSS REFERENCE TO RELATED APPLICATIONS

This application is a continuation of U.S. patent application Ser. No. 14/387,248, filed Apr. 12, 2013, in the name of Wojcik, et al., entitled MODULAR ACCESSORY SLEEVE FOR PORTABLE RADIOGRAPHIC DETECTORS, which is itself a 371 National Stage Application of earlier filed PCT Application PCT/US2013/0036302 filed Apr. 12, 2013 entitled MODULAR ACCESSORY SLEEVE FOR PORTABLE RADIOGRAPHIC DETECTORS, in the name of Wojcik, et al., which claims the benefit of U.S. Provisional application U.S. Ser. No. 61/623,641, filed on Apr. 13, 2012, entitled ACCESSORY SHELL FOR PORTABLE RADIOGRAPHY DETECTORS in the name of Wojcik et al., which is hereby incorporated herein by reference in its entirety.

FIELD OF THE INVENTION

The application generally relates to digital x-ray imaging methods/system, and more specifically, to methods and/or systems for medical imaging systems that use digital radiography (DR) detectors, and more particularly to a modular accessory package or housing for a portable DR detector.

BACKGROUND

Portable radiographic detectors are used with many varied radiographic systems (e.g., in room, mobile radiographic systems, portable radiographic systems, NDT systems) at many varied examination locations field use, under bedridden patients), at many varied conditions. There is a need for improved modular accessory housing or kits for portable radiographic detectors.

SUMMARY OF THE INVENTION

An aspect of this application is to advance the art of medical digital radiography.

Another aspect of this application is to address, in whole or in part, at least the foregoing and other deficiencies in the related art.

It is another aspect of this application to provide, in whole or in part, at least the advantages described herein.

An aspect of this application is to provide methods and/or apparatus embodiments to address and/or reduce disadvantages caused by the use of portable radiography detectors and imaging apparatus and/or methods using the same.

Another aspect of this application is to provide methods and/or apparatus embodiments to include capability in a base DR detector without implementing in the base DR detector cost/weight/complexity/capability that is used for a limited set of DR applications.

Another aspect of this application is to provide methods and/or apparatus embodiments to provide a modular approach to an accessory shell for a portable DR detector that can accessorize highly valued features for various applications.

Another aspect of this application is to provide methods and/or apparatus embodiments to provide a modular approach to an accessory shell for a portable DR detector that can variously selectively implement a subset of modular functionality to a base DR detector for various corresponding applications.

In accordance with one embodiment, the present invention can provide a modular accessory housing for a portable digital radiographic detector including a closable case, a power and signal distribution apparatus to provide power or communication for plurality of accessories mountable to the case, and at least two of a first device positionable in the sealable case to maintain a surface temperature of an inserted detector within a prescribed temperature range; a selectable additional wireless external communication system different from a wireless communication system provided to a detector; a tracking device configured to externally repeatedly report a current detector location of when powered by an attached detector; and a synch generator unit mounted to the sealable case to match exposure timing with patient cardiac or respiratory movement and configured to communicate movement information through an attachable detector.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DESCRIPTION OF EXEMPLARY EMBODIMENTS

The following is a description of exemplary embodiments of the invention, examples of which are illustrated in the accompanying drawings. Wherever possible, the same reference numbers will be used throughout the drawings to refer to the same or like parts.

For simplicity and illustrative purposes, principles of the invention are described herein by referring mainly to exemplary embodiments thereof. However, one of ordinary skill in the art would readily recognize that the same principles are equally applicable to, and can be implemented in, all types of radiographic imaging arrays, various types of radiographic imaging apparatus and/or methods for using the same and that any such variations do not depart from the true spirit and scope of the application. Moreover, in the following description, references are made to the accompanying figures, which illustrate specific exemplary embodiments. Electrical, mechanical, logical and structural changes can be made to the embodiments without departing from the spirit and scope of the invention. In addition, while a feature of the invention may have been disclosed with respect to only one of several implementations/embodiments, such feature can be combined with one or more other features of other implementations/embodiments as can be desired and/or advantageous for any given or identifiable function. The following description is, therefore, not to be taken in a limiting sense and the scope of the invention is defined by the appended claims and their equivalents.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. Where they are used, the terms "first", "second", and so on, do not necessarily denote any ordinal or priority relation, but may be used for more clearly distinguishing one element or time interval from another.

Digital detectors for medical digital radiography (DR) applications are well known, and are used for capturing digital medical x-rays.

The requirements for detectors that are being used in bucky vs. those being used in portable or field use are different and can be well served by a common detector with optional accessories. Embodiments of an accessory shell for portable radiographic detectors can provide a system solution for portable DR detectors and can implement or address a set of capabilities through a set of modular accessory attachments and inherent capabilities. Embodiments of an accessory shell for portable radiographic detectors can include a flexible enclosure that can depend on the detector body for structural shape, a disposable low cost shell with providing environmental protection but with reduced shock protection, full environmental robustness (e.g., MIL STD) provide x-ray exposure technique latitude, and/or combinations thereof. In one embodiment, the accessory shell can be closable or sealable. For example, the accessory shell can provide a modular approach that can adaptively accessorize highly valued features independently for various applications.

Various arrangements are described in FIGS. 1A-4 and/or in the arrangements shown below.

Several radiographic applications require environmental robustness and x-ray exposure technique latitude:
  Field use at temperatures from −40° to 140° F.
  Water resistance from bodily fluids (medical) and rain NDT)
  Withstands drops from 4 feet (e.g., MIL STD)
  Backscatter control from poorly collimated/pointed x-ray sources as well as higher energy beams.
  Accommodation of source-detector alignment instruments.
  A handle to improve ergonomics.
  Structure to attach source-detector alignment aids.
Certain exemplary accessory shell embodiments can provide: Handle, Grid (removable), Back Scatter (removable), Alternate radio (space allocation only), Tool Free Design, Robust Surface, Alternate image transport (e.g., Flash card, space alloc only), Compatible Tether, Easy Battery Access; Environmental Seal (water proof), Tube-Grid Alignment, Detector Location, Dual Energy Sync, Extra Battery; Increase Bending Strength/Resistance, Point Loading Capacity, Additional Shock/drop protection, High Speed Port, Info Display, Thermal Range Extension, Inductive Battery Charger, Backwards System compatibility.

Accessory shell embodiments can be a sealable flexible enclosure such as but not limited to a zip-lock bag with bumpers, back pockets, and an attached handle that houses power and electronics when necessary.
  Depends on the detector body for structural shape.
  Treats weight as a primary design attribute.
  Connects power/communications from enclosed internal detector to outside connector, retaining water resistance.
    Alternative is to route communications and power to battery and radio in handle.
  Accommodates a selection of accessories:
    Snap-on grid
    Additional backscatter shield in back pocket
    Source alignment aid instruments
    Temperature controller with portable flat panel detector (FPD) battery and insulated blanket
Certain exemplary accessory shell embodiments can provide:
  High image quality
  Low cost
  Light weight
  Disposability (cheap vacuum formed plastic shell)
  Scratch and abrasion protection of FPD surfaces
  Surface treatment to increase gripping friction
  Drop-shock and weight bearing durability
  Fast image access and cycle time
  Fast availability from cold start
  Long battery charge life
  Reliable operation
  Fast and easy movement/registration between various host systems
  Support of dual energy and tomosynthesis
  Abuse sensing
Non-Bucky Imaging Needs:
  Source to detector alignment aids.
  Fluid and particle tolerance.
  High backscatter tolerance due to poor exposure technique/alignment.
  Attitude sensing
  Location tracking.
  Roaming, "non-802.11", proprietary point-to-point connectivity option.
  Integrated objectives are to include as much capability in a base DR detector without burdening all units with cost/weight/complexity that is only useful for a limited set of applications. Another objective is to provide a modular approach that can accessorize highly valued features for various applications.

In certain exemplary embodiments, a portable DR detector accessory kit/sleeve can provide:
  1. Continued compatibility with commercially available film DR cassette accessory devices:
    a. Slip on grids.
    b. Protective bags.
    c. Positioning stands/holders.
    d. Protective shells for high weight bearing exams.
  2. New snap-on handle that is light weight, with cavities to accommodate:
    a. Additional PoE connected radio such as UWB or alternative "non-802.11" for mobile.

b. Optional USB or PoE powered accessories such as pulse oximeter, position locators, audio alarms for unintended out-of-range transport or anti-theft warning. (USB provided from PoE to USB converter).

3. New accessory shell with handle that accepts the various sized cassettes, has high fluid/particle resistance and allows several options:
   a. Additional PoE connected radio such as UWB or alternative "non-802.11" for mobile.
   b. Optional USB or PoE powered accessories as noted above.
   c. Snap-on grid.
   d. Source-to-grid alignment aid electronics.
   e. Backscatter absorbing panel.
   f. Mechanical features that interface with position holding devices (orthopedic, veterinary, cross-table stands, kick-stand and robot grippers for NDT-security).
   g. A reduced power consumption, local radio (e.g. ZigBee) for wake-up and exposure synchronization when using "Enterprise wireless".

Additional exemplary Accessory Shell embodiments can provide:

Fluid and particle resistant (sealable) enclosure with integral handle and features for snap-on grid, back pocket for additional backscatter shielding, additional bumpers, and detachable positioning devices such as stands.

Includes the magnetic tether connector, running PoE (Power over Ethernet), to additional radio and/or other accessories.

Passes the tether connection to second connector outside of shell housing to enable interface with other Ethernet or charge circuit connections.

An alternative construction could include thermal insulation, a temperature controller and material (e.g., Peltier sheet) for extreme temperature tolerance.

Figure 1A:
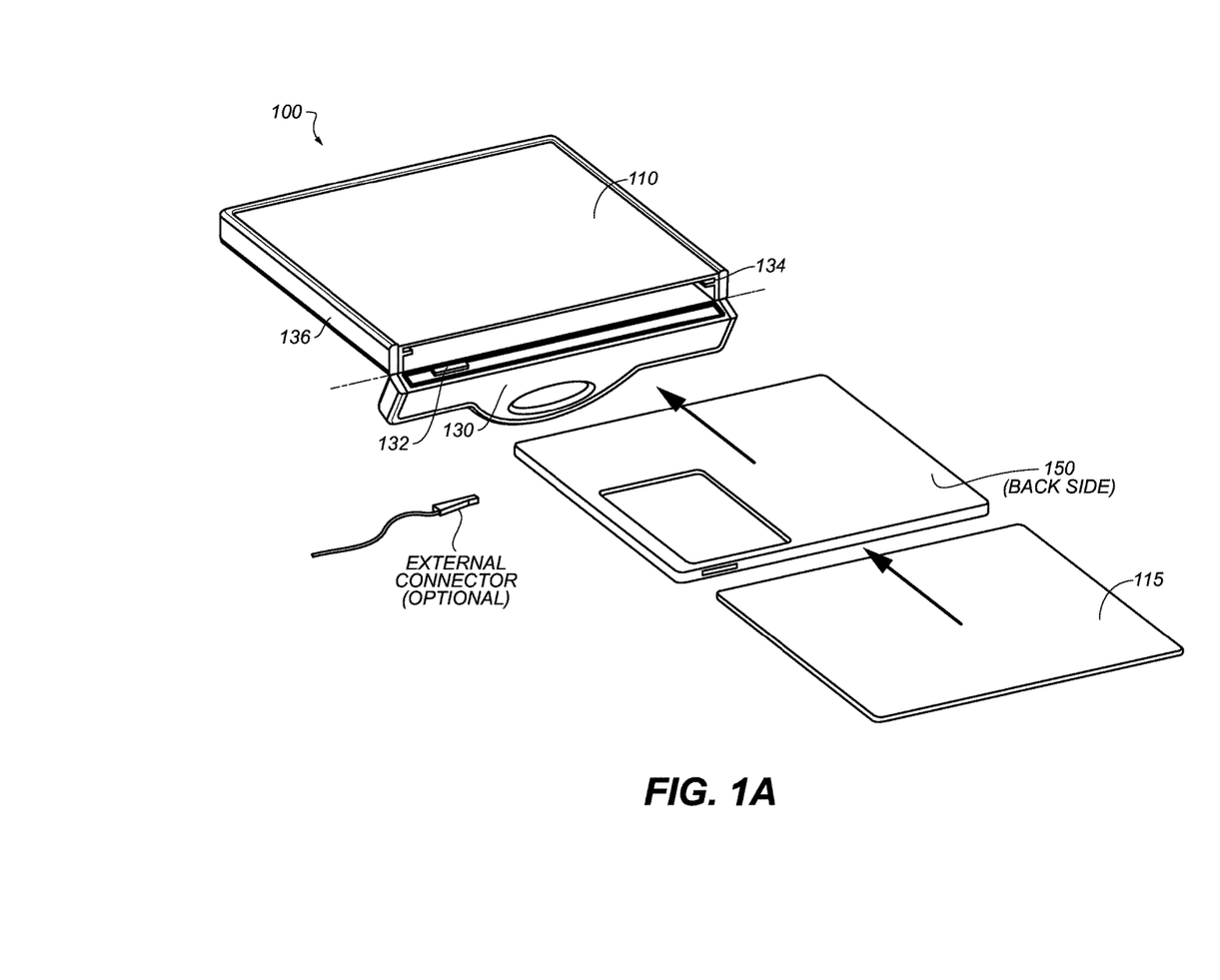
FIGS. 1A-1C are diagrams that show an exemplary embodiment of a modular accessory container for a portable radiographic detector according to the application.
Figure 1B:
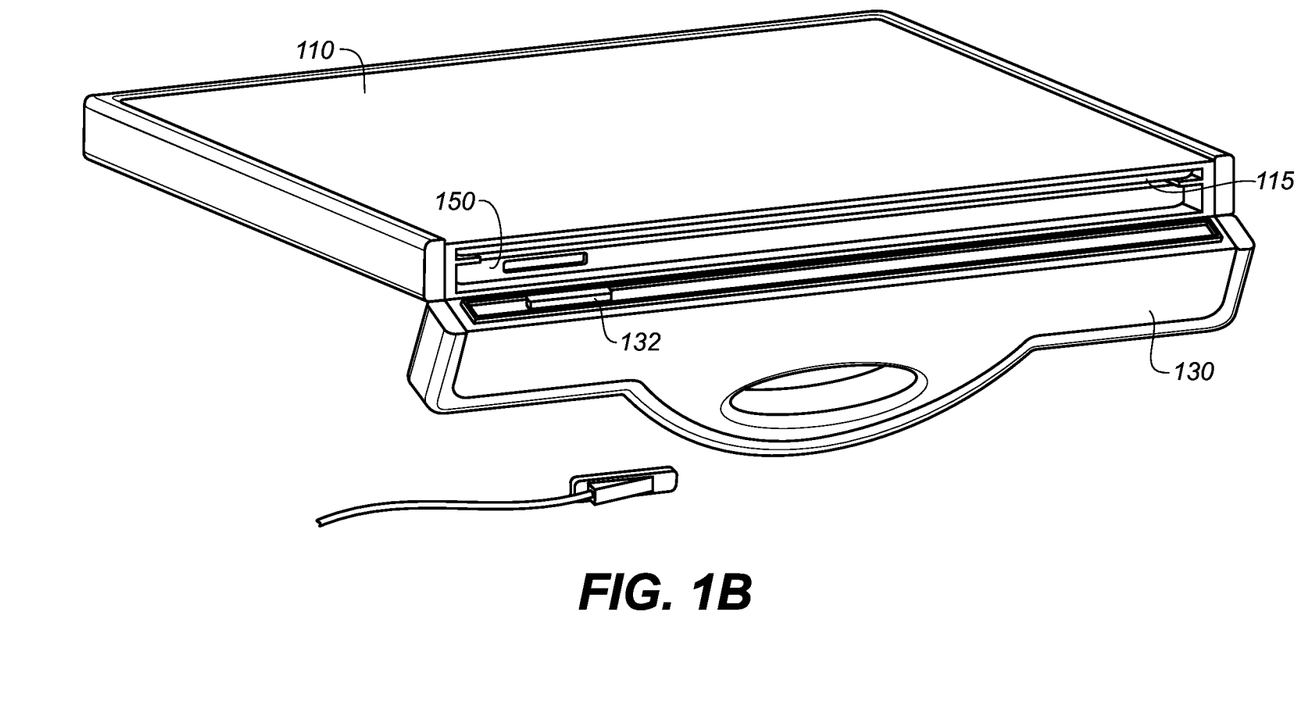
Figure 1C:
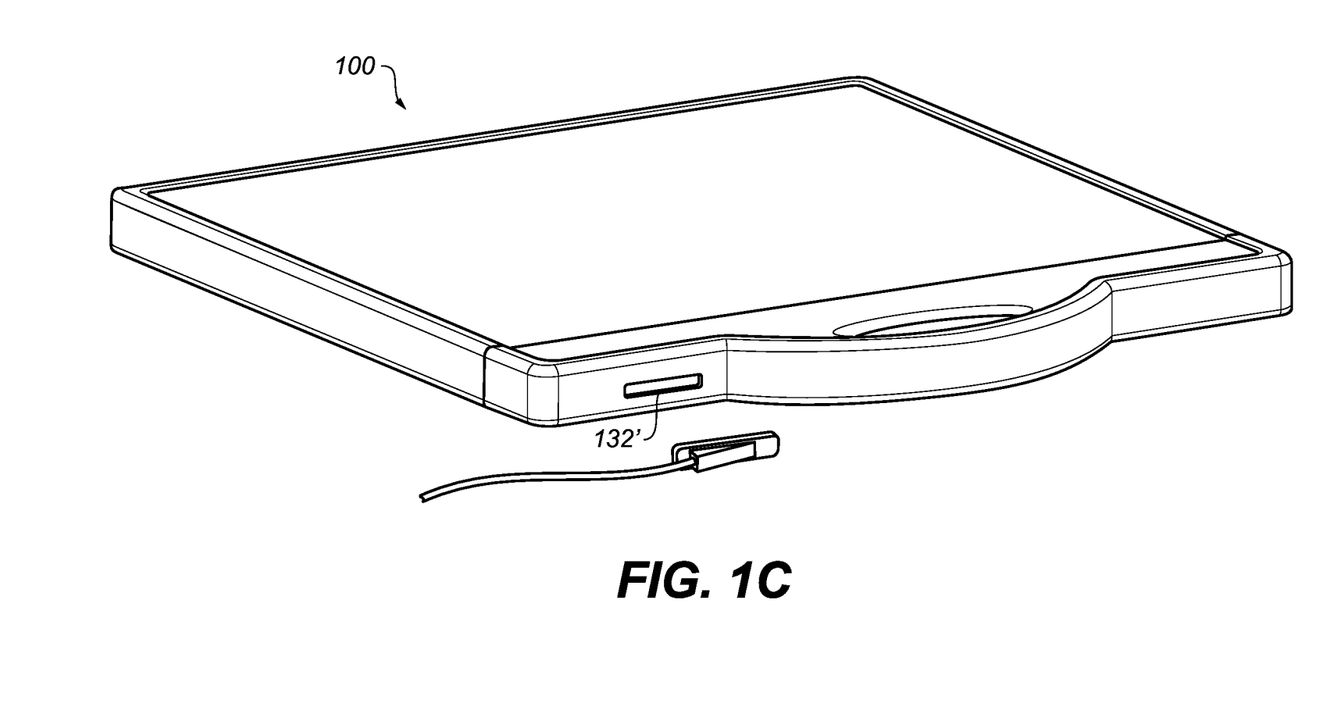

FIGS. 1A-1C are diagrams that show an exemplary embodiment of a modular accessory container for a portable DR detector according to the application. As shown in FIG. 1A, a modular accessory container 100 for a portable DR detector can include an environmental shell (e.g., case) 110. The modular accessory container 100 can selectively include a plurality of accessory functions (e.g., variously described herein) selected responsive to a use (e.g., specific imaging application such as but not limited to gen rad, CBCT or fluoroscopy) or field environment and radiographic imaging requirements to be performed. As shown in FIG. 1A, the environmental shell 110 can be a fluid and particle resistant (e.g., sealable, closable, or have one or more open surfaces) enclosure and can include a handle 130 (e.g., integral, attachable), connector 132 (e.g., power and/or communications) for connection to an inserted or mounted detector 150 that can provide an externally exposed connector 132', one or more recesses, mounts, or pockets such as back pocket 134 e.g., for additional backscatter shielding 115 or not illustrated optional temperature control (e.g., internal), and additional bumpers 136.

In one embodiment, a temperature control unit can provide or be mounted in the modular accessory container 100 to touch or be nearby one side or one or more surfaces of the detector 150. Further, the temperature control unit can be configured to cool or heat (e.g., responsive to a control signal or bias applied to the temperature control unit) a surface of the detector using a single position (e.g., without being moved). In one embodiment, the temperature control unit can maintain a selected temperature or temperature range for the inserted detector that can be dependent on a detector operating mode. For example, a first larger temperature range can be selected for a dual energy (e.g., first) operating detector mode and a second smaller temperature range can be selected for a more sensitive tomosynthesis (e.g., second) operating detector mode. In one embodiment, the temperature control unit can be passive (e.g., insulating sheet or sleeve) used at a patient's bed, self-powered or powered by a mounted detector.

Figure 2:
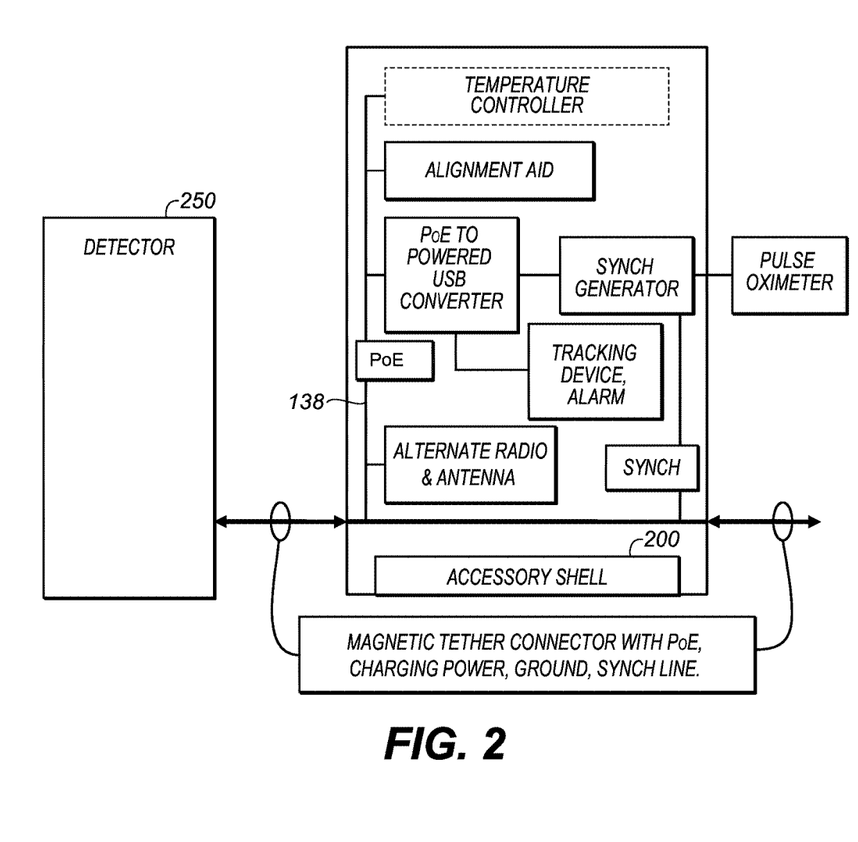
FIG. 2 is a functional block diagram that shows another exemplary embodiment of a modular accessory container from selectable accessories for a portable radiographic detector according to the application.

FIG. 2 is a diagram that shows another exemplary embodiment of a modular accessory container for a portable radiographic detector according to the application. As shown in FIG. 2, a selectable set of accessories can be operatively coupled to a power/communication bus 138 or network of a modular accessory shell or kit 200. In one embodiment, the power/communication bus 138 can provide PoE (Power over Ethernet) to additional radio and/or other accessories. As shown in FIG. 2, modular accessory shell 200 accessories can include temperature controller, alignment aids, additional wireless communication systems such as PoE connected radio such as UWB or alternative "non-802.11" for mobile, additional power converters, USB or PoE powered accessories such as pulse oximeter (e.g., patient movement sensor) including synch generator, tracking/position locators, audio alarms for unintended out-of-range transport or anti-theft warning. (USB provided from PoE to USB converter).

In one embodiment, a synch generator unit mounted to an attachable DR detector via the modular accessory container to match x-ray exposure timing generator or x-ray source) with patient cardiac or respiratory movement detected by a sensor (e.g., pulse oximeter) and configured to communicate movement information (e.g., to a controller of an associated radiographic imaging apparatus or controller of the x-ray source) through the attachable detector for controlling active patient imaging. The detector can use wired or wireless communication to transfer the movement information. The synch generator can analyze movement data (e.g., heartbeat, breathing, physical movement) in order to determine when the patient movement is at the same relative position (e.g., at rest between heartbeats, breath held/released) and thereby provide exposure timing for multiple exposure examinations (e.g., dual energy).

In one embodiment, a tracking device mounted to the modular accessory container can externally repeatedly report a current detector location when powered by an attached detector. In one embodiment, only one of associated radiographic imaging apparatus can include additional hardware to monitors a plurality of remote detectors for location or status using corresponding tracking devices. Alternatively, a central location (e.g., remote or local) can monitor a plurality of remote detectors for location or status using the corresponding powered tracking devices. In addition, a plurality of error conditions can be provided by a one of a plurality of prescribed timing sequences of communications of the tracking devices.

In one embodiment, accessories for the modular accessory shell 200 can use power supplied from a detector 250 rather than requiring an additional battery for these accessory devices. As shown in FIG. 2, the user can just recharge replace the detector 250 battery rather than dealing with two or more separate energy sources. Alternatively, one or more additional battery can be located in the accessory shell 200 rather than the detector 250, or in both locations to improve total energy capacity.

The battery (or batteries) can be recharged through a single tether connection, or through a non-contact charge circuit that couples to the detector or accessory shell.

Figure 3A:
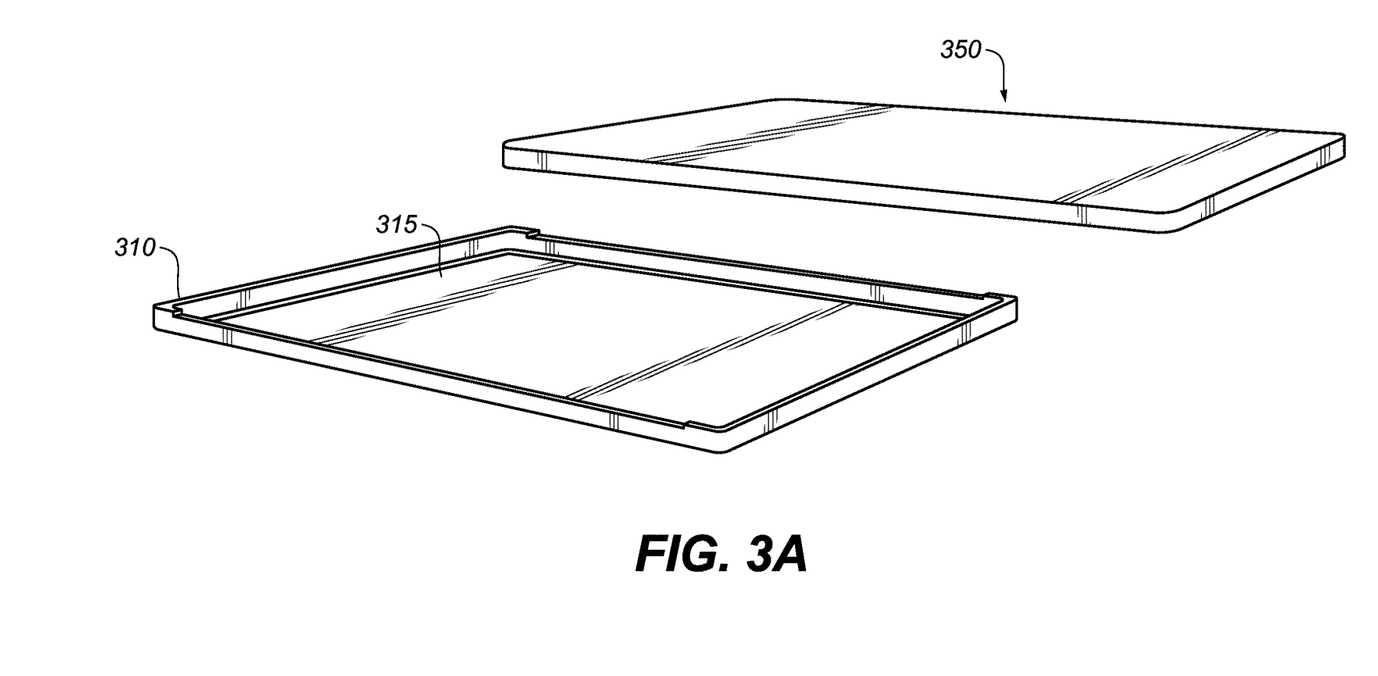
FIGS. 3A-3F are diagrams that show exemplary embodiments of a modular accessory container for a portable radiographic detector according to the application.
Figure 3B:
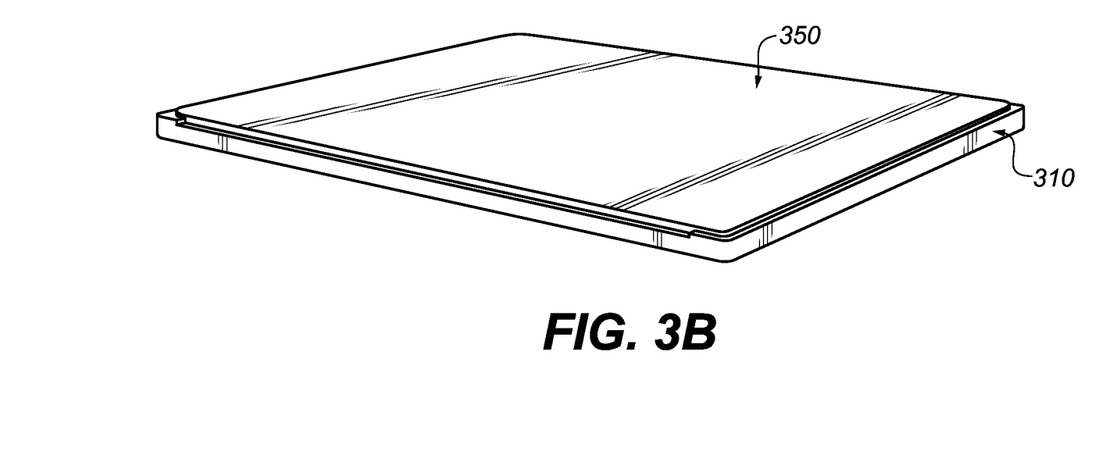

In one embodiment, very low cost accessory shell can provide a means to attach or hold an anti-scatter material or a sheet of anti-scatter lead to a back of a portable radiographic detector. FIG. 3A is a diagram that shows an exemplary embodiment of a modular accessory container for a portable radiographic detector according to the application. As shown in FIG. 3A, an accessory shell 310 with anti-scatter material 315 can be quickly and readily attached to a portable radiographic detector 350 without requiring difficult alignment or latching devices. The accessory shell 310 likewise can be quickly and easily removed from the radiographic detector 350 as shown in FIGS. 3A and 3B using, for example, felt pads that provide increased friction between the shell 310 (e.g., plastic) and the detector 350. This allows the back accessory shell 310 to be quickly removed, for example, to allow access to the back of the detector 350 housing when the detector battery (not shown) needs to be replaced.

It can also be beneficial to use the accessory shell 310 without anti-scatter material to protect the back surface of the portable radiological detector from scratches and abrasion. In one embodiment, the accessory shell can be a vacuum formed plastic shell. Vacuum formed plastic material thickness can be made very thin, e.g., on the order of 15 to 20 mils, so the plastic accessory shell will not appreciably add to the overall thickness of the detector 350, and accordingly, the accessory shell 310 can be used with the portable detector 350 in standard radiological equipment such as in Bucky drawers without interference.

It is also possible to place the back cover accessory shell 310 without anti-scatter material 315 over the (e.g., top and/or bottom) portable detector 350 to protect the top and/or bottom surface of the detector. Further, since the accessory plastic shell 310 is very low cost the accessory shell 310 can be disposed of when worn from use and can be easily replaced with a new accessory shell 310 of the same type.

Figure 3C:
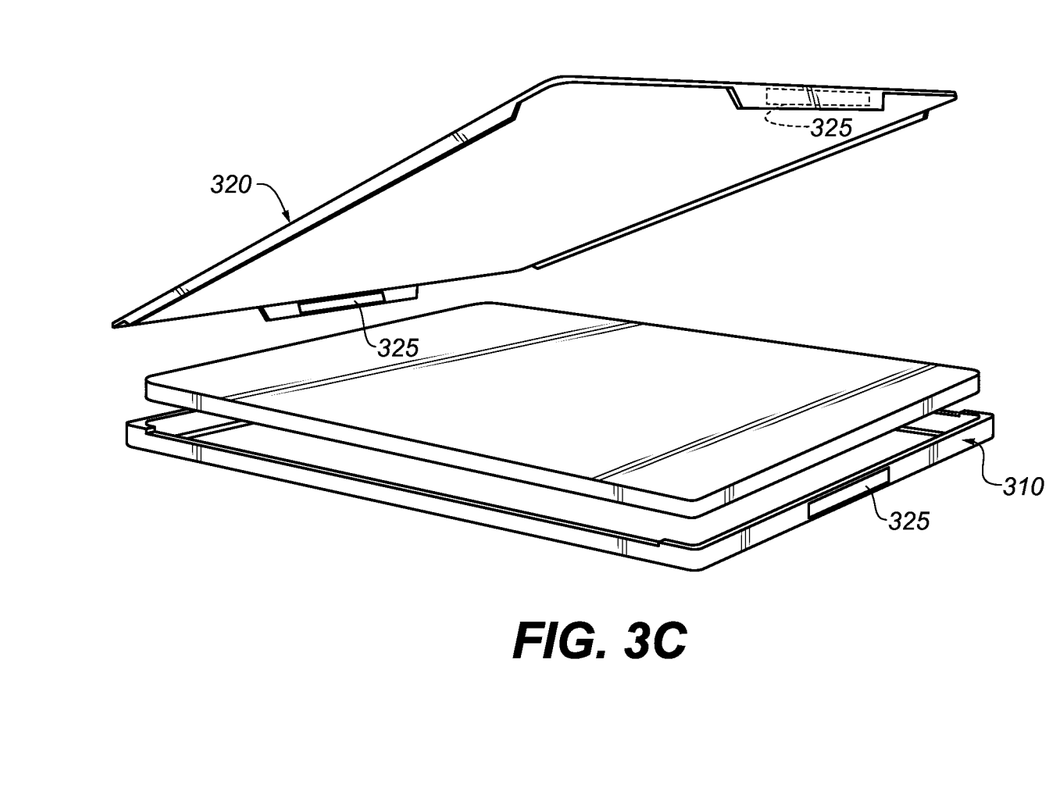

In one exemplary embodiment, in addition to the accessory shell 310 that covers the back surface, another complementary low cost accessory shell can be used to cover the top surface. As shown in FIG. 3C, a top cover accessory shell 320 in conjunction with the back shell can enclose and/or protect up to the entire portable radiological detector 350 from surface abrasion and damage to due normal wear and tear. The top cover accessory shell 320 can be removably fastened and held to the back surface accessory shell 310. In one embodiment, the vacuum shell can be formed from more than two connectable pieces. In one embodiment, fasteners 325 can securely, but removably affix the top cover accessory shell 320 to the accessory shell 310. Fasteners 325 (e.g., Velcro of Velcro strips) can allow quick attachment and removal of the top accessory shell 320 to the bottom shell 310.

Figure 3D:
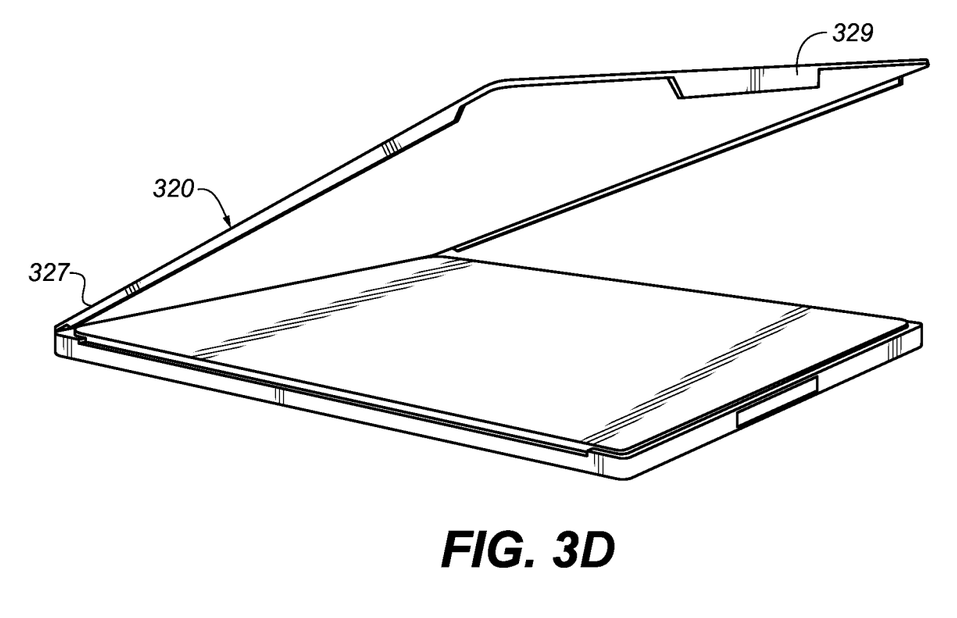

In one embodiment, the top accessory shell 320 can have a flexible flap 327 at one end of the shell as shown in FIGS. 3C and 3D. The flexible flap 327 can serve as a hinge for the top cover shell allowing for quick and easy insertion of the portable radiological detector into the top and bottom accessory shells. In one embodiment, an opposing end of the shell 320 can have a flexible flap 329. Such an exemplary flexible flap arrangement can also be used to keep the top shell 320 and the bottom shell 310 halves connected together as a unit when not used (e.g., with a detector 350).

Figure 3E:
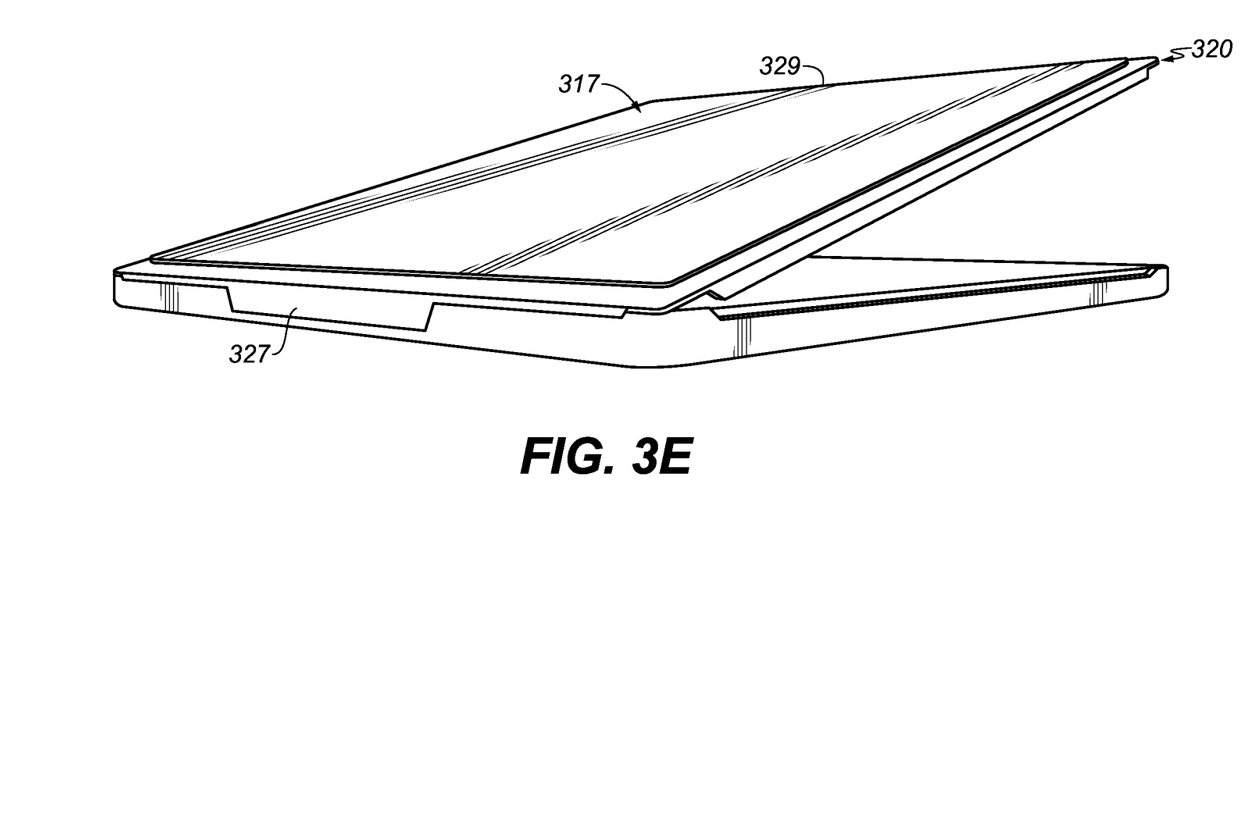

In one embodiment, an accessory shell can also include an a scatter grid. As shown in FIG. 3E, an anti-scatter grid 317 can be attached to an outer surface of the accessory shell 320. The grid 317 can be securely but removably fixed to the accessory shell 320 (e.g., with a low tack force double side pressure sensitive adhesive (PSA)). Such an attachment can serve to hold the anti-scatter grid 317 firmly to the top accessory shell 320 and because the adhesive has a low tack force, the grid 317 can be easily separated from an accessory shell such as when the accessory shell 320 becomes worn out.

Figure 3F:
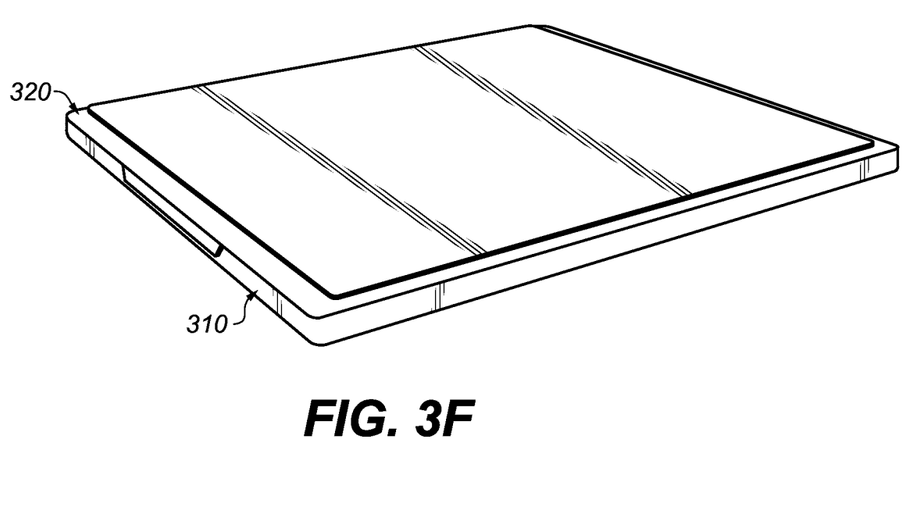

FIG. 3F is a diagram that depicts the portable radiological detector 350 enclosed in a top and bottom accessory shell pair 310, 320 with an anti-scatter grid 317 attached to the outer surface of the top shell 320.

The versatility of a wireless portable radiological detector includes its ability to be carried from one location to another throughout a medical facility. A portable radiological detector is typically carried around by medical staff members who use the detector to image patients in different locations. Due to frequent handling there is an increased risk that an expensive portable detector might be dropped and damaged. One way to reduce this risk is to provide a non slip surface treatment to the outer surfaces of a detector. However, this is usually impractical because non slip surfaces can interfere with the placement of the detector under a patient. Also, a non slip surface over time will tend to wear out during normal usage and the non slip performance will degraded.

To reduce the risk of dropping a portable radiological detector, medical staff can insert the portable detector into an accessory shell treated with a non slip surface material. When it is desired to place the portable detector under a patient the non slip accessory shell can be removed. Once the radiological images are taken the accessory shell can be placed back on the detector for carrying to another location. Since the accessory shell is made inexpensively it can be disposed of and replaced with a new one when the non slip surface treatment becomes degraded.

In one exemplary embodiment, it is advantageous to have an accessory shell that has had a non slip surface treatment applied to the accessory shell. The accessory shell can look like the one pictured in FIG. 3B and could likewise be made of a low cost vacuum formed plastic with a non slip surface treatment applied to its outer surfaces.

Figure 4:
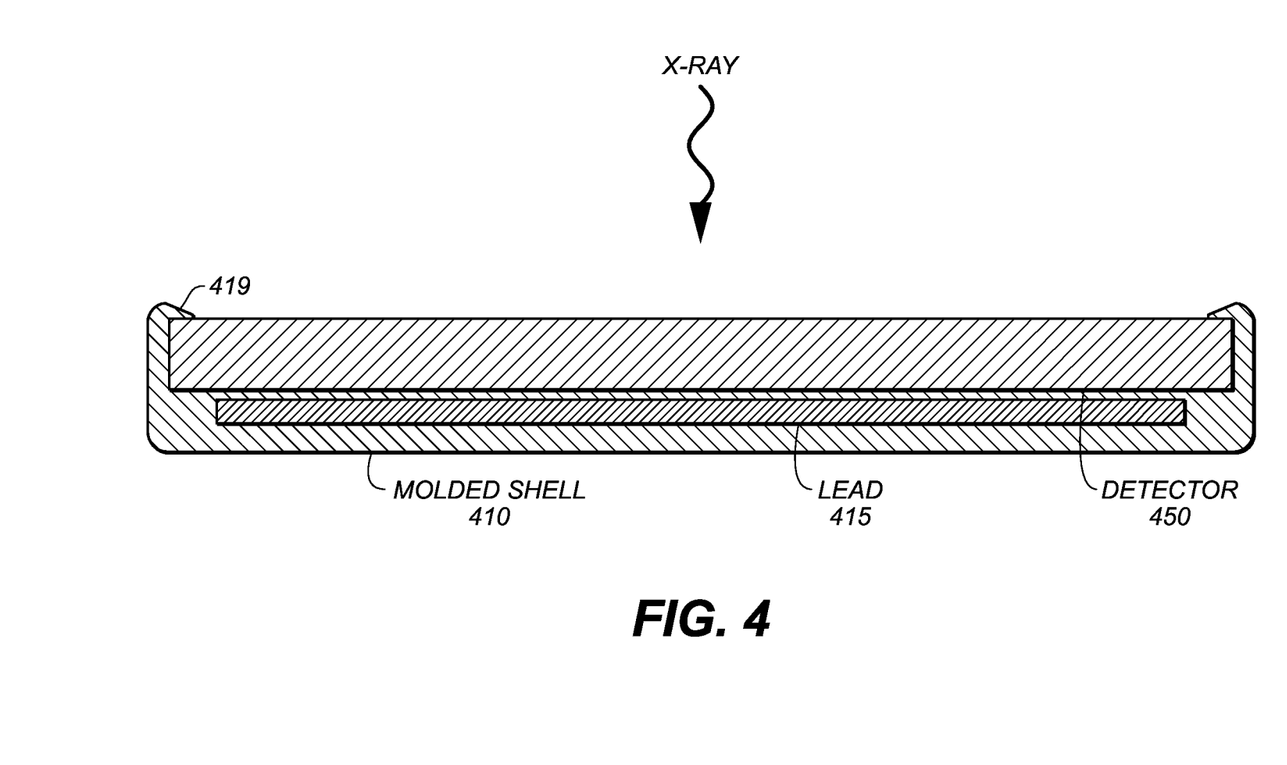
FIG. 4 is a diagram that shows still yet another exemplary embodiment of a modular accessory container for a portable radiographic detector according to the application.

FIG. 4 is a diagram that shows an exemplary embodiment of a modular accessory container for a portable radiographic detector according to the application. As shown in FIG. 4, in one embodiment, an accessory sleeve or an accessory shell 410 can be a one-sided shell or a back cover shell (e.g., one-sided shell can include/exclude backscatter grid 415 or anti-scatter grid (not shown)). There are situations where a portable radiographic detector 450 can use only a one-sided shell 410 or a back cover shell (e.g., a top cover to the detector 450 or detector assembly can be avoided, because of added weight and x-ray absorption). As shown in FIG. 4, in one embodiment, a seal or lip 419 can be used with an open sided shell (described herein) that can be elastic and to "lock" the detector 450 in place, and/or to provide a seal (e.g., liquid) against the detector 450 (e.g., a carbon fiber top surface or cover).

In one embodiment, a handle can be included as part of an attachable/detachable accessory shell or back accessory shell.

Exemplary embodiments herein can be applied to digital radiographic imaging panels that use indirect detectors (e.g., separate scintillating screen) and/or direct detectors (e.g., an array of pixels comprising an X-ray absorbing photoconductor and a readout circuit).

It should be noted that while the present description and examples are primarily directed to radiographic medical imaging of a human or other subject, embodiments of apparatus and methods of the present application can also be applied to other radiographic imaging applications. This includes applications such as non-destructive testing (NDT), for which radiographic images may be obtained and provided with different processing treatments in order to accentuate different features of the imaged subject.

Embodiments of radiographic imaging systems and/methods described herein contemplate methods and program products on any computer readable media for accomplishing its operations. Certain exemplary embodiments accordingly can be implemented using an existing computer processor, or by a special purpose computer processor incorporated for this or another purpose or by a hardwired system.

Consistent with exemplary embodiments, a computer program with stored instructions that perform on image data accessed from an electronic memory can be used. As can be appreciated by those skilled in the image processing arts, a computer program implementing embodiments herein can be utilized by a suitable, general-purpose computer system, such as a personal computer or workstation. However, many other types of computer systems can be used to execute computer programs implementing embodiments, including networked processors. Computer program for performing method embodiments or apparatus embodiments may be stored in various known computer readable storage medium (e.g., disc, tape, solid state electronic storage devices or any other physical device or medium employed to store a computer program), which can be directly or indirectly connected to the image processor by way of the internet or other communication medium. Those skilled in the art will readily recognize that the equivalent of such a computer program product may also be constructed in hardware. Computer-accessible storage or memory can be volatile, non-volatile, or a hybrid combination of volatile and non-volatile types.

It will be understood that computer program products implementing embodiments of this application may make use of various image manipulation algorithms and processes that are well known. It will be further understood that computer program products implementing embodiments of this application may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with computer program product implementing embodiments of this application, are not specifically shown or described herein and may be selected from such algorithms, systems, hardware, components and elements known in the art.

This application claims the benefit of U.S. Provisional Application No. 61/623,641, filed Apr. 13, 2012, which is hereby incorporated by reference in its entirety.

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations/embodiments, such feature can be combined with one or more other features of the other implementations/embodiments as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only. The scope of the invention is indicated by the appended claims, and all changes that come within the meaning and range of equivalents thereof are intended to be embraced therein.

The invention claimed is:

1. A modular accessory housing configured to receive a portable digital radiographic detector, the detector comprising top and bottom surfaces, four sides all connected to the top and bottom surfaces, and a first wireless communication system, the modular accessory housing comprising:
   a closable case configured to enclose the sides and at least one of the top and bottom surfaces of the detector; and
   a second wireless external communication system different from the first wireless communication system.

2. The modular accessory housing of claim 1, wherein the first and second wireless communication systems include a local wireless communication system for communicating synchronization data with an x-ray generator and a standard wireless communication system for communicating over a wide area network.

3. The modular accessory housing of claim 2, further comprising:
   a first device positionable in the closable case to maintain a surface temperature of an inserted detector within a prescribed temperature range.

4. The modular accessory housing of claim 3, wherein the prescribed temperature range is dependent on a detector operating mode, and wherein the first device is configured to maintain the surface temperature within a first larger temperature range for a first operating mode of the detector and to maintain the surface temperature within a second smaller temperature range for a second operating mode of the detector.

5. The modular accessory housing of claim 4, wherein the first operating mode of the detector is a dual energy mode and the second operating mode of the detector is a tomosysnthesis mode.

6. The modular accessory housing of claim 1, wherein the local wireless communication system comprises a local area receiver for detector wake-up and exposure synchronization and a reduced power consumption as compared to the standard wireless communication system.

7. The modular accessory housing of claim 2, further comprising:
   a tracking device configured to repeatedly transmit a current detector location when powered by an attached detector.

8. The modular accessory housing of claim 2, further comprising:
   a synch generator unit mounted to the closable case to match exposure timing with a patient cardiac or respiratory movement and configured to wirelessly transmit information associated with said movement.

9. The modular accessory housing of claim 2, wherein the closeable case comprises an image display and an image processor to process image data received from the detector.

10. The modular accessory housing of claim 2, wherein the closeable case comprises a recessed pocket to receive a backscatter shield.

11. The modular accessory housing of claim 2, further comprising:
  a power and signal distribution assembly having a first connector for connecting to an inserted detector and a second connector at an exterior of the closable case to provide electronic communication access to the inserted detector.

12. The modular accessory housing of claim 2, wherein the closable case comprises six sides, one of the six sides is configured to open to receive the detector therethrough, and wherein said one of the six sides is configured to close to enclose all six sides of the detector within the modular accessory housing.

13. A modular accessory housing configured to receive a portable digital radiographic detector, the detector comprising a first wireless communication system and a second wireless communication system different from the first wireless communication system, the modular accessory housing comprising:
  a closable case configured to enclose the detector; and
  a power and signal distribution assembly electrically connected to the detector to provide power and electronic communication between the detector and one or more accessories mounted to the closable case.

* * * * *